United States Patent [19]
Skladnev et al.

[11] Patent Number: 5,852,494
[45] Date of Patent: Dec. 22, 1998

[54] APPARATUS FOR CHECKING THE CALIBRATION OF OPTICAL PROBES

[75] Inventors: Victor N. Skladnev, Vaucluse; Richard L. Thompson, Killarney Heights, both of Australia; Irwin Wunderman, Mtn. View, Calif.

[73] Assignee: Polartechnics Limited, Sydney, Australia

[21] Appl. No.: 819,107

[22] Filed: Mar. 17, 1997

[51] Int. Cl.⁶ .................................. A61B 5/00; G01J 1/02
[52] U.S. Cl. ............................................................ 356/243
[58] Field of Search ............................ 356/243; 600/477

[56] References Cited

U.S. PATENT DOCUMENTS

| | | | |
|---|---|---|---|
| 4,250,394 | 2/1981 | O'Connor | 356/340 |
| 4,322,164 | 3/1982 | Shaw et al. | 356/243 |
| 4,796,633 | 1/1989 | Zwirkoski | 356/243 |

*Primary Examiner*—Richard A. Rosenberger
*Attorney, Agent, or Firm*—Gottlieb Rackman & Reisman, P.C.

[57] ABSTRACT

An apparatus which permits an analytical probe to be calibrated by pressing the tip against a block of material of controlled characteristics. A transparent elastomer is used into which has been incorporated a light-scattering material. Elastomer calibrators may also be made part of a preassembled probe component such as a disposable sheath. In that case the turbid elastomer is assembled on the tip with the other components of the sheath and is removed after calibrating the system and before the probe put into use. An additional film of flexible polymer having optical characteristics analogous to the material to be detected by the probe may be placed on top to simulate the structure of the material that is to be measured.

11 Claims, 4 Drawing Sheets

APPARATUS FOR CHECKING THE CALIBRATION OF OPTICAL PROBES

FIELD OF THE INVENTION

This invention concerns a system for calibrating and checking instruments that measure the optical characteristics of tissue by measuring the proportion of impressed radiation that is backscattered by the material under examination. Such instruments typically emit light of a variety of wavelengths into the material to be measured and detect the backscattered light. They need to be calibrated and to be checked frequently. This invention employs a number of materials and systems to achieve this calibration.

BACKGROUND OF THE INVENTION

An increasing number of instruments are being developed to measure the optical characteristics of materials by detecting the radiation that is backscattered. For example the medical profession often needs to have an objective assessment of the health of the tissue of a patient. The patient may have suffered tissue damage as a result of accidental or deliberate trauma as for example during a surgical operation. The patient may also be suffering some other more persistent irritation as a result, for example, of being confined to bed which can lead to bed sores. It is valuable for a medical practitioner to be able to tell in advance the type of treatment that would benefit the patient. Probes able to make these measurements are coming onto the market.

Errors in diagnosis by such probes can have serious consequences so it is important that they be frequently checked for drift or damage that could lead to these errors. Previous attempts to make these checks have been highly susceptible to the manner of use by the operator. For example, the placement of the probe at a short distance from a reflective surface can produce a reading which is indicative of the behavior of the probe but is vulnerable to serious error. The distance between the reflector and the probe tip is extremity critical and impractically so. The conditions of the test surface must also be controlled for a number of characteristics. Any material on the surface which affects the amount of specularly reflected light will invalidate the readings. It must in general be kept scrupulously clean.

To overcome the problems indicated above it is known to use a liquid for calibration purposes. Two types are commonly used. One of these is a liquid suspension of biological origin. It is unstable with time and not reproducible from batch to batch. The second is from a suspension of solid spheres of precise dimensions. They are expensive and need agitation to maintain uniformity. Neither of these calibration materials is practical for routine field testing of instruments.

BRIEF DESCRIPTION OF THE INVENTION

It is an object of the present invention to provide a method and apparatus for calibrating and checking probes which employ backscattered radiation to measure the optical characteristics of a material. Such probes may for example be employed to provide an objective identification of the tissue types on a patient including the presence of pre-cancerous and cancerous activity.

According to one aspect of the present invention there is disclosed an apparatus which permits the probe to be calibrated by simply pressing the tip against a block of material of controlled characteristics. In this form of calibrator a transparent elastomer is used into which has been incorporated a light-scattering material. The light-scattering material can be any one of a number of whiteners such as titanium dioxide, barium sulphate, or magnesium oxide. The concentration of whitener is varied to suit the particular turbidity that is needed. The elastomer can be, for example, a polyurethane rubber or a silicone rubber. Any type of transparent or translucent elastomer is able to meet the short term needs of this invention. Long term stability is another matter dealt with below.

Elastomer calibrators may also be made part of a preassembled probe component such as a disposable sheath. In that case the turbid elastomer is assembled on the tip with the other components of the sheath and is removed after calibrating the system and before the probe put into use.

Another form of calibrator comprises a turbid elastomer as above and on top of that is placed a film of flexible polymer which is intended to simulate the structure of the material that is to be measured. The latter may for example be a layer of precancerous cells on cervical tissue. The layer of polymer film that is placed over the elastomer should have optical characteristics analogous to the material to be detected by the probe. In the case of cervical intra-epithelial neoplasia, the cervical tissue becomes covered with a layer of abnormal cells. A calibrator intended to check the performance of a device that is to detect this layer of cells may provide more reliable diagnoses if it is calibrated in an environment equivalent to that pertaining during the diagnostic probing, that is, by using a layered calibrator.

The above embodiments have major advantages in terms of practicability over the liquid calibrators that have been available previously. Nevertheless it may still be appropriate to employ a liquid calibration material. Liquids have advantages when there is some uncertainty about the quality of contact between the probe tip and the test material. The liquid used in this embodiment of the invention comprises a latex made from carboxylated styrene butadiene copolymer. This latex is highly stable and can be made in a variety of concentrations by water dilution.

A further embodiment of the invention employs the use of dyes to modify the optical characteristics of the test material. This can be important where the subject material for the probe to diagnose is colored. The use of a white test material may not detect errors in the operation of the probe. In the case of human tissue the inclusion of a red dye renders the test material more like the tissue to be diagnosed by simulating the presence of blood.

DETAILED DESCRIPTION OF PREFERRED EMBODIMENTS

Figure 1:
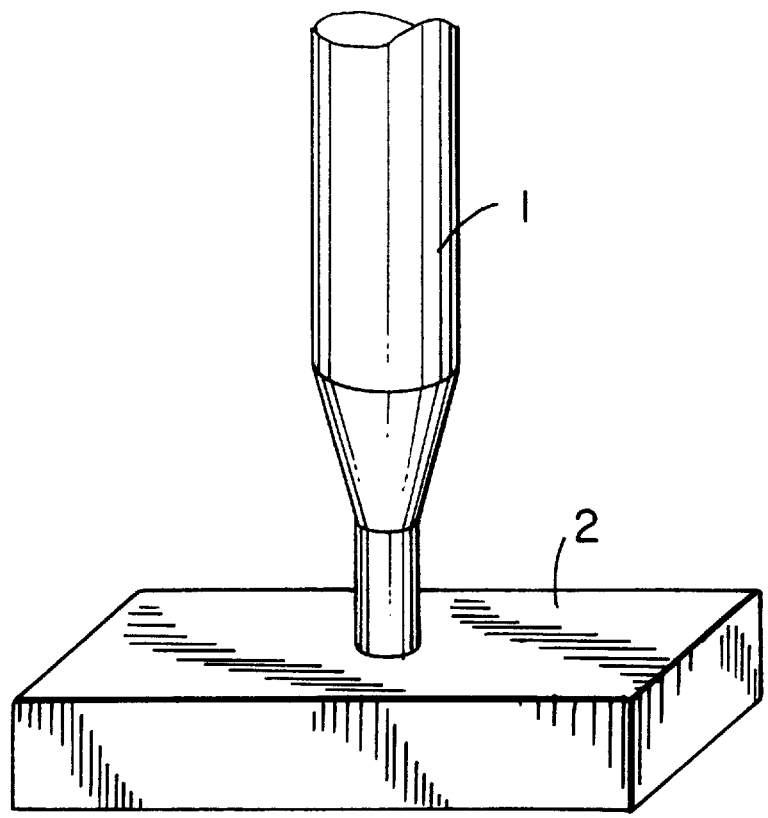
FIG. 1 is an illustration of a probe being tested on a calibrator.

FIG. 1 shows a perspective view of the probe tip 1 being held against the surface of the turbid elastomer block 2. Such probes are described in copending application Ser. No. 08/332,830 and employ optical fibers to convey radiation to and from the probe tip. Further details are found in the aforesaid application, the disclosure of which is incorporated herein by reference. In addition calibrators of the present invention are useful in connection with hybrid probes such as disclosed in a copending application filed this date entitled "Hybrid Probe For Tissue Type Recognition" Ser. No. 08/819,912 and for certain endocervical probes disclosed in our copending application filed this date entitled "Apparatus For Tissue Type Recognition Within A Body Canal," Ser. No. 08/818,930 and incorporated herein by reference. The invention is also useful in conjunction with various sheaths that are used in connection with probe bodies and that provide optical and electrical pathways through the sheath. Such sheaths are disclosed in our copending applications filed this same date entitled "Sheathed Probes For Tissue Type Recognition" Ser. No. 08/823,660 and "Sheath For A Side View Probe", both of which disclosures are incorporated herein by reference.

In each of these examples, the hardness of the elastomer should be matched to the consistency of the material on which the probe is to be employed. For example, probes intended for use on human tissues are designed to operate on material with hardness in the range 10 to 50 Durometer A. Elastomers in this range can be made from polyurethanes and silicones. Whitening agents are commercially available for both these resins and typically contain titanium dioxide although other white pigments can be used.

Since the calibrators will have to remain stable for long periods, of the order of years, it is advantageous to formulate them from silicones. Other elastomers can change color with time, which will change the readings of the instrument.

Figure 2:
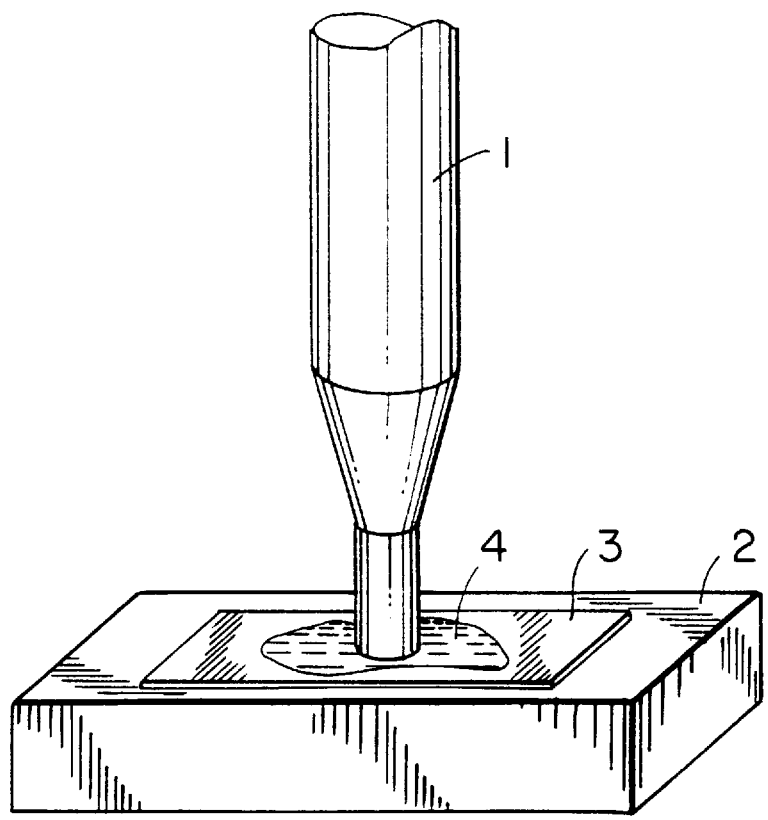
FIG. 2 is an illustration of another embodiment that includes the use of a plastic film between the probe tip and the test material.

FIG. 2 illustrates an embodiment of the invention that includes a plastic film 3 between the tip of the probe and the test material block. A liquid 4 to aid matching of the refractive indices is usually employed in this case to avoid light loss by reflections at the interfaces between air and the solids.

The plastic film used for this embodiment needs to be flexible enough to conform to the tip of the probe without allowing gaps to occur. The addition of the liquid 4 which may for example be water will fill minor gaps and restore the reliability of the readings. Polythene film may be employed in this embodiment but even when thin it may be relatively stiff compared to the elastomer block. Gaps as indicated can occur.

If the film thickness needs to be raised to simulate accurately the geometry of the test situation, softer plastics or elastomers may be used. The maximum thickness of stiffer plastics such as polythene that can be used is around 10 micrometers. The suitability of the chosen material can be determined by checking the reproducibility of the readings.

The plastic film 3 needs to be chosen with a number of criteria in mind. The stiffness has been described above. The thickness will depend on the geometry of the situation to be simulated. The film may need to contain an appropriate amount of whitener or light scattering material. The color may need to be adjusted by adding dyes.

Figure 3:
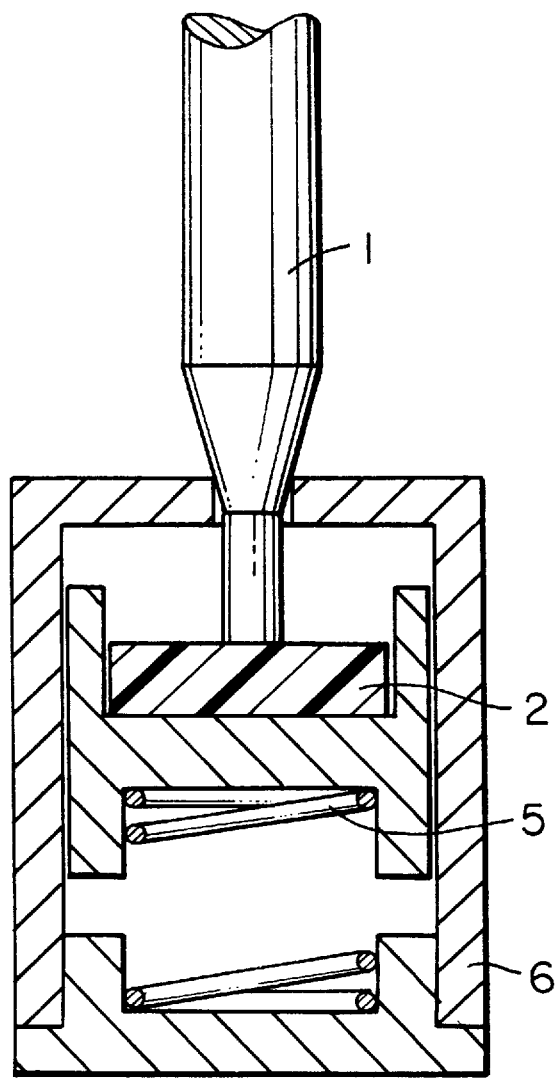
FIG. 3 is an illustration of a calibration test unit with a spring.

FIG. 3 shows another embodiment of the invention. In this embodiment the block of elastomer 2 is pressed against the end of the probe 1 with a controlled force by means of a spring 5 contained within the body 6 of the calibrator unit. It has been found that operators are not always reliable in their ability to apply a suitable force to the probe when performing a calibration. This embodiment ensures that the appropriate force is applied to achieve reliable optical contact between the probe tip and the elastomer. The required force is preset by the initial compression force achieved by deflecting the spring during assembly of the unit. In use, a probe is inserted into the calibrator unit and pressed down until the spring 5 is deflected.

Figure 4:
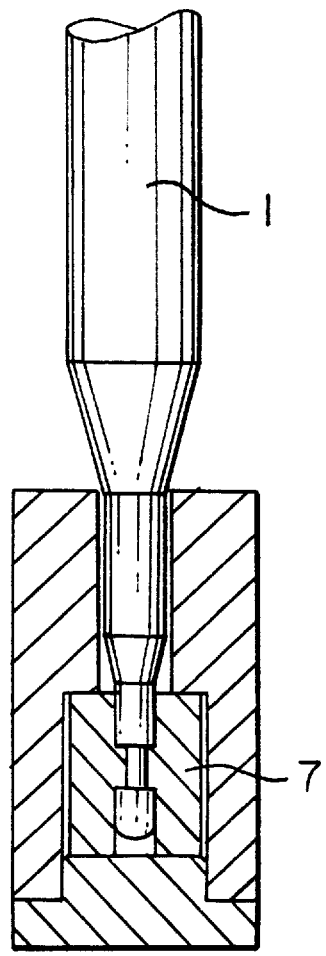
FIG. 4 is an illustration of a calibration test unit fitted to a side viewing probe.

The embodiment shown in FIG. 4 is intended for use with side viewing probes such as the endocervical probe. Such probes are used to examine and diagnose the material inside the walls of tubes or cavities. In this embodiment the calibrator tube 7 is slid over the base of the probe tip until it has covered the optical section completely. There are clear advantages achieved by constructing the calibrator from an elastomer which will deflect to allow the entry of the probe while ensuring good optical contact between the probe surface and the calibrator material. A rigid calibrator would not achieve this optical contact because of surface irregularities and the need to avoid harsh contact forces that would scratch the optical surface of the probe.

Although the invention has been described in terms of preferred embodiments its full scope is determined by reference to the following claims allowing the full scope of equivalents to be substituted for any of the specifically enumerated elements.

What is claimed is:

1. An apparatus for identifying whether tissue under examination has been physiologically changed comprising
   a probe that emits radiation to the tissue under examination and receives radiation backscattered from said tissue, said probe having
      an active tip intended for the measurement of optical properties of materials by the measurement of the proportion of backscattered radiation from the material, said active tip comprising
         a light emitter configured to irradiate said tissue;
         a detector configured to receive radiation backscattered by said tissue;
   a calibrating apparatus for the calibration of said probe, comprising
      a turbid elastomer blocks
      a polymer film interposed between the probe tip and the block of turbid elastomer, wherein said polymer film conforms to the tip of the probe when said probe is compressed between said polymer film and said block,
   wherein said calibrating apparatus causes a portion of the radiation to be back scattered.

2. An apparatus as in claim 1 in which the turbid elastomer is colored with a dye to simulate the material to be measured.

3. The apparatus of claim 2, wherein said dye comprises a whitening agent.

4. The apparatus of claim 3, wherein said whitening agent comprises titanium dioxide.

5. An apparatus as in claim 1 further comprising a spring of known modulus indicating by compression the pressure exerted against said elastomer block.

6. The apparatus of claim 1, further comprising a suspension of a polymer latex in the range of 0.1 to 3% solids in a liquid into which is placed the tip of a probe for calibration.

7. The apparatus of claim 1, wherein said elastomer block comprises one or more silicones.

8. The apparatus of claim 1, wherein a liquid is interposed between said polymer film and the active tip of the probe.

9. The apparatus of claim 8, wherein the index of refraction of said liquid is matched to the index of refraction of said polymer film.

10. The apparatus of claim 1, wherein said polymer film is polythene having a thickness of less than about 10 micrometers.

11. An apparatus for identifying whether tissue under examination has been physiologically changed comprising a side view probe that emits radiation to the tissue under examination and receives radiation backscattered from said tissue, said probe having an active region of said probe located at least in part away from the tip of the probe and intended for the measurement of optical properties of materials by the measurement of the proportion of backscattered radiation from the material, said active region comprising light emitters configured to irradiate said tissue;

detectors configured to receive radiation backscattered by said tissue;

a calibrating apparatus for the calibration of said probe, comprising a turbid elastomer block covering said active region completely and deflecting to provide optical contact between the active surface and the elastomeric block, wherein said calibrating apparatus causes a portion of the radiation to be back scattered.

* * * * *